United States Patent [19]
Santaniello et al.

[11] Patent Number: 5,856,569
[45] Date of Patent: Jan. 5, 1999

[54] PROCESS FOR PRODUCING VALPROIC ACID

[75] Inventors: Mosè Santaniello, Nettuno; Carlo Alberto Bagolini, Roma; Agostino Uttaro, Gaeta; Silverio Fontana, Latino Scalo, all of Italy

[73] Assignee: Sigma-Tau Industrie Farmaceutiche Riunite S.p.A., Rome, Italy

[21] Appl. No.: 941,722

[22] Filed: Oct. 1, 1997

[30] Foreign Application Priority Data

Oct. 10, 1996 [IT] Italy ................................ RM96A0688

[51] Int. Cl.$^6$ .................................................. C07C 53/128
[52] U.S. Cl. ............................................................ 562/606
[58] Field of Search ............................................. 562/606

[56] References Cited

U.S. PATENT DOCUMENTS

| | | | |
|---|---|---|---|
| 3,325,361 | 6/1967 | Eugene et al. | 562/606 X |
| 4,155,929 | 5/1979 | Chignac et al. | 558/369 |
| 5,101,070 | 3/1992 | Yamamoto et al. | 562/606 |
| 5,344,975 | 9/1994 | Zeiler | 562/606 |
| 5,672,746 | 9/1997 | Nau et al. | 562/606 X |

OTHER PUBLICATIONS

Database CAPLUS on STN® International, Chemical Abstracts Service, (Columbus, Ohio), Accession No. 1990:590753, Zydzil et al. PL 136499 B1, Nov. 30, 1987, abstract, 1990.

*Primary Examiner*—Michael G. Ambrose
*Attorney, Agent, or Firm*—Oblon, Spivak, McClelland, Maier & Neustadt, P.C.

[57] ABSTRACT

A process for making valproic acid from an alkyl alkanoylacetate is disclosed. The alkyl alkanoylacetate is reacted with an n-propyl halide in a biphasic system in the presence of a base and a phase transfer catalyst. The product mixture is acidified to convert the resulting valproate salt into valproic acid.

15 Claims, No Drawings

PROCESS FOR PRODUCING VALPROIC ACID

The present invention relates to an improved process for the preparation of valproic acid.

Valproic acid (2-propylpentanoic acid; di-n-propylacetic acid) and its sodium and magnesium salts have long since been utilized in therapy as anti-epileptic and anti-convulsant drugs.

The conventional process which is still used for the preparation of valproic acid (see Labaz's patents GB 1522450, GB 1529786 and U.S. Pat. No. 4,155,929) substantially comprises dialkylating ethyl cyanacetate with propyl bromide in the presence of sodium ethoxide thus obtaining ethyl α,α-dipropyl cyanacetate which is converted, in a basic enviroment, to dipropyl acetonitrile which by alkaline hydrolysis gives valproic acid.

The reaction scheme of this process is the following:

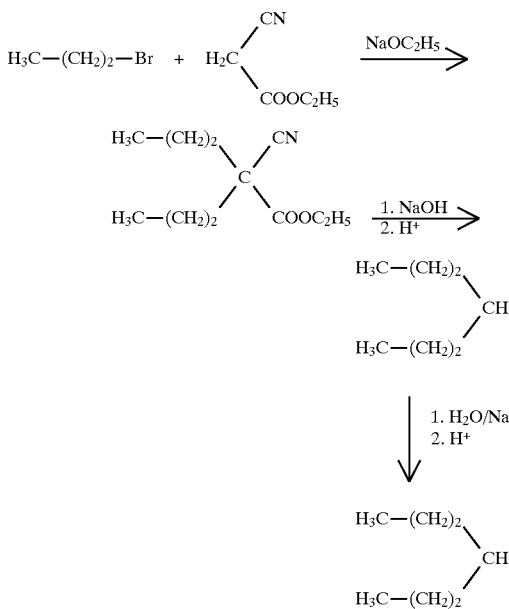

This conventional process presents serious drawbacks which can be summarized as follows:

(a) sodium ethoxide entails the use, particularly on the industrial scale, of a substantially anhydrous reaction enviroment and brings about complex pollution problems;

(b) sodium ethoxide is completely used up during the dialkylation of ethyl cyanacetate;

(c) the decarboxylation step of ethyl α,α-dipropylcyanacetate requires drastic operating conditions, high temperatures and prolonged reaction times;

(d) also the conversion of the nitrile derivative to valproic acid requires drastic hydrolysis conditions, high temperatures (about 200° C.) and prolonged reaction times (more than six hours).

As a consequence of the aforesaid disadvantages, it is apparent that the conventional process is remarkably costly because of the nature of the reactants, the energy consumption and the need of utilizing devices and technologies commensurate to the safety and pollution problems inherently brought about by the process itself.

It is an object of the present invention to provide an improved process for producing valproic acid which overcomes all the foregoing drawbacks. In particular, it is an object of the present invention to provide a process wherein the use of alkaline alkoxides, and particularly of sodium ethoxide, is completely avoided. Further advantages of the improved process according to the invention shall be apparent from the detailed description thereof here below.

The improved process for producing valproic acid according to the present invention is shown in the following reaction scheme:

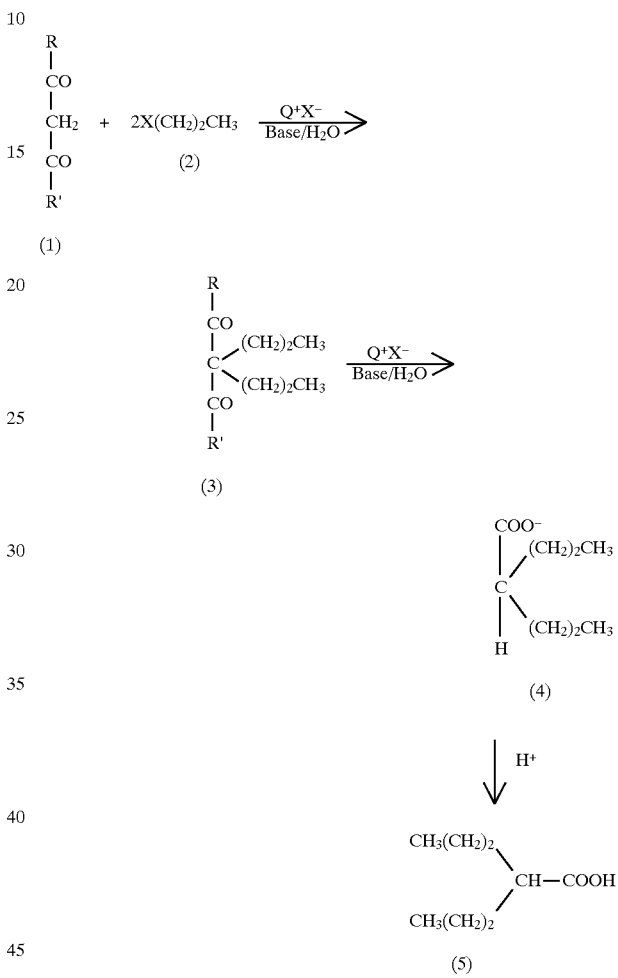

wherein:
R is an alkoxy group having 2–5 carbon atoms;
R' is an alkyl group having 1–4 carbon atoms, and
$Q^+X^-$ indicates a phase-transfer catalyst wherein $Q^+$ is quaternary ammonium or phosphonium and $X^-$ is any suitable anion, preferably a halogenide anion.

The process comprises the following steps:
(a) dialkylating a beta-ketoester (1) having formula

R
|
CO
|
$CH_2$
|
CO
|
R'

(1)

wherein:

R is an alkanoyl group having 2–5 carbon atoms; and R' is an alkyl group having 1–4 carbon atoms with a propyl halogenide (2) having formula $$X(CH_2)_2CH_3 \qquad (2)$$

wherein: X is chlorine, bromine or iodine, preferably bromine by reacting a biphasic system consisting of
(i) an aqueous phase comprising a base, preferably NaOH, and a phase-transfer catalyst $Q^+X^-$ wherein $Q^+$ is quaternary ammonium or phosphonium and $X^-$ is any suitable anion, preferably halogenide, and
(ii) an organic phase comprising the beta-ketoester (1) and the propyl halogenide (2), wherein the (2):(1) molar ratio is from 5:1 to 15:1, preferably 10:1, at 60°–80° C. (inner temp.) for at least 25 hours, thus obtaining, following removal of (2) excess, a biphasic reaction mixture whose organic phase is comprised of the dialkyl-beta-ketoester (3)

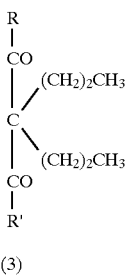

(3)

(b) reacting the mixture obtained in step (a) which comprises the dialkylester (3), in the presence of an alkali, preferably NaOH, at 70°–90° C., preferably 80° C., for at least 20 hours, thus obtaining an aqueous phase comprising the salt (4)

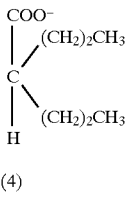

(4)

(c) acidifying the aqueous phase comprising the salt (4) of step (b) at pH 1–3, thus obtaining valproic acid (5)

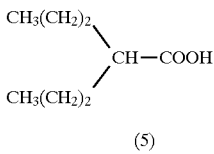

(5)

In the beta-ketoester (1), R is preferably an alkoxy group having 2–3 carbon atoms and R' is an alkyl group having 1–2 carbon atoms. A particularly preferred ester (1) is the ethyl ester of acetoacetic acid.

The propyl halogenide (2) is preferably propyl bromide. Suitable phase-transfer catalysts $Q^+X^-$ wherein $Q^+$ is quaternary ammonium or phosphonium and $X^-$ is any suitable anion shall be apparent to the average-skilled expert in organic synthesis. Examples of suitable $Q^+X^-$ catalysts are:

tetrabutylammonium bromide, tetrabutylammonium bisulphate, benzyltriethylammonium chloride, benzyltributylammonium bromide, tetrabutylphosphonium bromide and benzyltriphenylphosphonium chloride.

A particularly preferred $Q^+X^-$. Catalyst is tetrabutylammonium bromide (TBABr).

When step (b) is completed, it is economically advantageous to recover the catalyst which can thus be reutilized. Catalyst recovery is achieved by extracting the reaction mixture with an organic solvent, preferably a halogen-containing solvent, such as e.g. dichloethane, chloroform or methylene chloride; concentrating the organic phase thus obtained which is taken up with a precipitating organic solvent, such as e.g. toluene or ethyl acetate, thus obtaining a precipitate consisting of the catalyst which, following filtration, is wholly recovered.

The following non-limiting example shows the preparation of valproic acid via the process of the present invention.

EXAMPLE

Preparation of valproic acid from the ethyl ester of acetoacetic acid 19.33 (0.06 moles of TBABr were added to a solution of 8 g (0.2 moles) of NaOH in 30 mL $H_2O$ and the resulting mixture was heated at about 80° C. till complete dissolution.

After cooling to 60° C., 61.5 (0.5 moles) of propyl bromide and 6.5 g (0.05 moles) of ethyl acetoacetate were contemporaneously added to the mixture. The resulting bi-phasic system was kept under vigorous stirring for 39 hours at 71° C. (inner temp.)

30.7 g (0.249 moles) of propyl bromide and a solution of 2.28 g (0.057 moles) of NaOH in 5 mL $H_2O$ were added and the resulting mixture was left to react under the aforesaid conditions for further six hours.

The excess of propyl bromide was distilled off and recovered, thus giving a biphasic reaction mixture whose organic phase consisted of ethyl-2,2-dipropyl acetoacetate, which was directly used in the subsequent reaction.

To this mixture comprising the ethyl-2,2-dipropyl acetoacetate a solution of 8 g (0.2 moles) of NaOH in 10 mL $H_2O$ was added ant the resulting mixture left to react at 80° C. (inner temp.) for 20 hours.

This end mixture was diluted with water and the catalyst was recovered via $CH_2Cl_2$ extraction. Following separation from the organic phase, the water phase was acidified at pH 1 wiht 33% HCl and extracted three times with ethyl acetate. It was then dehydrated with anhydrous $Na_2SO_4$ and concentrated to dryness yielding 3.1 g of valproic acid.

The organic phase was washed three times with water, then the pooled waters were acidified and extracted with ethyl acetate. The organic phase was dehydrated and concentrated to dryness yielding 0.9 g of valproic acid.

The catalyst was recovered by concentrating the organic phase ($CH_2Cl_2$) and diluting with ethyl acetate thus obtaining the formation of a white precipitate consisting of the catalyst which was filtered off.

G.C. Control: (end product) Rt=13.78

G.C.: (column: nucol 0.53 mm×30 m, program temp. 50° C. for 3 min. 50° C./min. till 170° C., 20 min. at 170° C., injec temp. 190° C., detector temp. 190° C., carrier gas: helium)

$H^1$NMR(CDCl$_3$): δ0.8 (6H,t,—CH$_2$CH$_2$C$\underline{H}_3$); 1.25(4H, m,—CH$_2$C$\underline{H}_2$CH$_3$); 1.5(4H,m,—C$\underline{H}_2$CH$_2$CH$_3$); 2.25 (1H,m,—C$\underline{H}$(CH$_2$CH$_2$CH$_3$)$_2$); 10.9(1H,s.b.—COO$\underline{H}$)

Gas chromatographic titre against inner standard=98%.

Both the novel and unobvious aspects and the remarkable practical and economical advantages afforded by the process of the present invention over the conventional process shall now be apparent to any expert in organic synthesis, particularly to the expert in industrial organic synthesis.

The conversion of the dialkyl-beta-ketoester (3) to the salt (4) (Claisen's inverse reaction) is not carried out according to the conventional method, i.e. in the presence of sodium methoxide or ethoxide and methanol or ethanol, but in the presence of a base (e.g. NaOH) and a phase-transfer catalyst (e.g. TBABr) which, unlike the alkaline alkoxide, is in practice wholly recovered. The remarkable advantages resulting from the elimination of reactants such as the alkaline alkoxides, have been described already.

Claisen's inverse reaction according to the invention lends itself to "fit" with the hydrolysis reaction of compound (3), so that both reactions are in practice carried out in a single step.

It is furthermore apparent that the whole process of the invention can be conducted as a continous sequence of operations, i.e. without isolating the reaction intermediates, but rather simply by adjusting the various operational conditions to the values suited for the specific step being carried out.

We claim:

1. A process for producing valproic acid, comprising:

(a) dialkylating a beta-ketoester represented by formula (1):

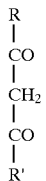  (1)

with a propyl halogenide represented by formula (2):

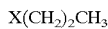  (2)

by contacting
   (i) an aqueous phase comprising water, a base and a phase-transfer catalyst represented by the formula $Q^+X^-$, and
   (ii) an organic phase comprising the beta-ketoester represented by formula (1) and the propyl halogenide represented by formula (2), wherein the molar ratio (2):(1) is from 5:1 to 15:1, at 60°–80° C. for at least 25 hours, followed by removing excess (2), to produce a reaction mixture comprising said aqueous phase and said organic phase, wherein said organic phase contains a dialkyl-beta-ketoester represented by formula (3):

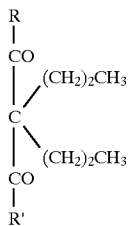  (3)

(b) contacting the reaction mixture from step (a) with an alkali at 70°–90° C. for at least 20 hours, to produce in said aqueous phase a salt represented by formula (4):

  (4)

(c) acidifying said aqueous phase to produce valproic acid represented by formula (5):

  (5)

wherein
   R is an alkoxy group having 2–5 carbon atoms;
   R' is an alkyl group having 1–4 carbon atoms;
   X is chlorine, bromine or iodine;
   $Q^+$ is quatenary ammonium or phosphonium; and
   $X^-$ is an anion.

2. The process of claim 1, wherein R is an alkoxy group having 2–3 carbon atoms and R' is an alkyl group having 1–2 carbon atoms.

3. The process of claim 2, wherein the ester represented by formula (1) is the ethyl ester of acetoacetic acid.

4. The process of claim 1, wherein the propyl halogenide represented by formula (2) is propyl bromide.

5. The process of claim 1, wherein $Q^+X^-$ is selected from the group consisting of tetrabutylammonium bromide, tetrabutylammonium bisulphate, benzyltriethylammonium chloride, benzyltributylammonium bromide, tetrabutylphosphonium bromide and benzyltriphenylphosphonium chloride.

6. The process of claim 1, wherein $Q^+X^-$ is tetrabutylammonium bromide (TBABr).

7. The process of claim 1, wherein X is bromine.

8. The process of claim 1, wherein the base in the aqueous phase is NaOH.

9. The process of claim 1, wherein $X^-$ is a halogenide.

10. The process of claim 1, wherein $X^-$ is chloride, bromide or bisulfate.

11. The process of claim 1, wherein $X^-$ is bromide.

12. The process of claim 1, wherein the alkali in step (b) is NaOH.

13. The process of claim 1, wherein excess (2) is removed by distillation.

14. The process of claim 1, wherein $Q^+$ is quaternary ammonium and $X^-$ is a chloride, bromide or bisulfate.

15. The process of claim 1, wherein
   X is bromine;
   $Q^+$ is quaternary ammonium;
   $X^-$ is a chloride, bromide or bisulfate;
   wherein the base in the aqueous phase is NaOH;
   the alkali in step (b) is NaOH; and
   excess (2) is removed by distillation.

* * * * *